US006465176B1

(12) United States Patent
Giordano et al.

(10) Patent No.: US 6,465,176 B1
(45) Date of Patent: Oct. 15, 2002

(54) METHOD FOR IDENTIFYING COMPOUNDS RNA/RNA BINDING PROTEIN INTERACTIONS

(75) Inventors: Tony Giordano, Phoenixville, PA (US); Deborah L. Beach, Wilmington, DE (US); Gretchen L. Temeles, Ardmore, PA (US)

(73) Assignee: Message Pharmaceuticals, Inc., Malvern, PA (US)

( * ) Notice: Subject to any disclaimer, the term of this patent is extended or adjusted under 35 U.S.C. 154(b) by 0 days.

(21) Appl. No.: 09/165,868

(22) Filed: Oct. 2, 1998

(51) Int. Cl.[7] ............................................... C12Q 1/68
(52) U.S. Cl. ...................... 435/6; 435/91.1; 435/91.2; 435/6; 935/77; 935/78; 530/350
(58) Field of Search .......................... 435/6, 91.1, 91.2; 935/77, 78; 530/350

(56) References Cited

U.S. PATENT DOCUMENTS

| | | |
|---|---|---|
| 5,534,408 A | 7/1996 | Green et al. |
| 5,543,499 A | 8/1996 | Brewer |
| 5,610,015 A | 3/1997 | Wickens et al. |
| 5,668,165 A | 9/1997 | Wuonola et al. |
| 5,677,131 A | 10/1997 | Wickens et al. |
| 5,776,502 A | 7/1998 | Foulkes et al. |

FOREIGN PATENT DOCUMENTS

| | | | | |
|---|---|---|---|---|
| EP | 405-980 | * | 1/1991 | ............... 435/91.42 |
| WO | WO 92/02228 | | 2/1992 | |
| WO | WO 92/05195 | | 4/1992 | |
| WO | WO 93/12234 | | 6/1993 | |
| WO | WO 94/09792 | | 5/1994 | |
| WO | WO 94/26890 | | 11/1994 | |
| WO | WO 97/09053 | | 3/1997 | |
| WO | WO 98/04923 | | 2/1998 | |
| WO | WO 98/37422 | | 8/1998 | |

OTHER PUBLICATIONS

Adams et al. Nature Genetics, vol. 4, pp. 256–267, Nov. 1993.*
Hillier et al. Genome Research. vol. 6, No. 9. pp. 807–828, Sep. 1996.*
Vieira et al. Proc. Nat'l. Acad. Sci. vol. 88, No. 4, pp. 1172–1176, Feb. 1991.*
Hillier et al. GenBank Accession No. N22791.*
Mosmann et al. Accession No. Q10207.*
Hillier et al. Accession No. H88835.*
Hillier et al. Accession No. T60217.*
Adams et al. Accession No. T07935.*
Lin et al., "Ribonucleoprotein organization of eukaryotic RNA. XXXI. Structure of the U1 small nuclear ribonucleoprotein," J. Mol. Biol. 180:947–960 (1984).
Malter, "Identification of an AUUUA–specific messenger RNA binding protein." Science 246:664–666 (1989).
Rouault, et al., "The iron–responsive element binding protein: a method for the affinity purification of a regulatory RNA–binding protein," Proc. Natl. Acad. Sci. USA 86:5768–6772 (1989).

Tan et al., "Costabilization of peptide and RNA structure in an HIV Rev peptide–RRE complex," Biochemistry 33:14579–14585 (1994).
Zaidi et al., "Nucleolin and heterogeneons nuclear ribonucleoprotein C proteins specifically interact with the 3'–untranslated region of amyloid protein prescusor mRNA" J. Biol. Chem 270(29):17292–17298 (1995).
Zaidi et al., "Multiple proteins interact at a unique cis–element in the 3' untranslated region of amyloid precursor protein mRNA," J. Biol. Chem. 269:(39) 24000–24006 (1994).
Adams et al., "Initial assessment of human gene diversity and expression patterns based upon 83 million nucleotides of cDNA sequence," Nature 377(28):3–17 (1995).
Database EBI 'Online!, "cDNAs from fetal heart," Database accession No. HSN4041 XP–002187015 (1996).
Database EBI 'Online!, "EST 17864 Aorta endothelial cells, TNF alpha–treated Homo sapiens cDNA 5' end similar to amyloid A4 beta subunit," Database accession No. HSZZ12916 XP–002187016 (1997).
Database EBI 'Online!, "Human STS SHGC–52109 sequence tagged site," Database accession No. HS1293668 XP–002187017 (1997).
Database EBI 'Online!, "EST96209 human testis Homo sapiens cDNA 5' end similar to amyloid beta A4 precursor protein, mRNA sequence," Database accession No. HS81110 XP–002187018 (1995).
Database EBI 'Online!, "Human colon 3' directed Mboi cDNA," Database accession No. HSGS04101 XP–002187019 (1994).
Database EBI 'Online!, "zo33h07.r1 Stratagene colon, Homo sapiens cDNA clone 5' similar to erbb–2 receptor, mRNA sequence," Database accession No. HSAA56178 XP–002187020 (1997).

* cited by examiner

*Primary Examiner*—W. Gary Jones
*Assistant Examiner*—Janell E. Taylor
(74) *Attorney, Agent, or Firm*—Clark & Elbing LLP; Kristina Bieker-Brady (57) ABSTRACT

Disclosed are nucleic acid sequences which, when present in an RNA molecule, bind to RNA binding proteins. These nucleic acid sequences are present in untranslated regions of certain mRNA. They can be used in assays to identify compounds that affect the interaction of RNA containing the nucleic acid sequence, such as the source mRNA, and RNA binding proteins. The disclosed nucleic acid sequences can also be used to identify RNA binding proteins that can interact with the sequences. An assay for identifying compounds that affect interaction of RNA containing one of the disclosed nucleic acid sequences and RNA binding proteins is also disclosed. The assay involves detecting interactions between RNA binding proteins and an RNA molecule containing one of the disclosed nucleic acid sequences in the presence of a test compound and in the absence of the test compound. A difference in the detected interaction in the presence and absence of the test compound indicates that the compound affects the interaction. The identified compounds can be used to affect the interaction of RNA binding proteins with mRNA containing the nucleic acid sequences or related sequences.

13 Claims, 3 Drawing Sheets

FIG. 1
IRE

METHOD FOR IDENTIFYING COMPOUNDS RNA/RNA BINDING PROTEIN INTERACTIONS

BACKGROUND OF THE INVENTION

The invention is in the area of screening assays for identifying compounds that can affect gene expression, and specifically for identifying compounds that affect interactions between RNA and RNA binding proteins.

The regulation of protein expression can occur at a number of levels: transcriptional, post-transcriptional, or post-translational. The modulation of protein expression is often critical for the treatment of disease. Recent work at modulating protein levels by altering transcriptional activity has resulted in preclinical research programs being established and licensing agreements being entered into. For example, Ligand Pharmaceuticals, Inc. (San Diego, Calif.) has entered into multiple drug discovery programs with large pharmaceutical companies based on their Signal Transducers and Activators of Transcription technology for use as anti-inflammatory, anti-cancer and hormone replacement therapies. In addition, Oncogene Science, Inc. (Uniondale, N.Y.) is using its proprietary gene transcriptional technologies to develop biopharmaceutical products for the treatment of cancer. Other companies, such as Signal Pharmaceuticals, Inc. (San Diego, Calif.) and Tularik, Inc. (San Francisco, Calif.) are developing small molecules that regulate transcription factors. While this approach holds promise, no compounds have yet to make it to clinical trials. The lack of specificity of transcription factors and requirement for nuclear localization are two concerns with this technology. In the first case, a drug affecting the binding of a transcription factor may affect transcription of many genes other than the target gene. In the second case, it is difficult to design a drug that both has the proper interaction with a targeted transcription factor and is transported into the nucleus where it exerts its effect. Inhibition of protein expression by targeting the RNA is an alternate approach involving antisense technology. The antisense technology has also generated much interest with several products in clinical trials (ISIS2105, ISIS2922 and ISIS2302). However, the major drawbacks with this approach are the cost of oligonucleotides, the ability to deliver the oligonucleotides into cells, and their inability to increase protein levels.

A major area of post-transcriptional regulation in eukaryotic cells involves the specific interaction of proteins with RNA. These RNA binding proteins (RBP) appear to mediate the processing of pre-mRNAs, the transport of mRNA from the nucleus to the cytoplasm, mRNA stabilization, the translational efficiency of mRNA, and the sequestration of some mRNAs. Recent studies have identified several RNA-binding motifs in a diversity of RBPs. The most common RNA binding protein motifs are the RNP motif, Arg-rich motif, RGG box, KH motif and double-stranded RNA-binding motif (for review see Burd and Dreyfuss, *Science* 265:615–621 (1994)). These motifs recognize both sequence and structure dependent RNA elements. In the case of the double-stranded RNA-binding motif, sequence recognition is unimportant. However, in addition to the double stranded structure, a positional effect for the double-stranded RNA may play a role in recognition (Bass, *Nucleic Acids Symposium* 33:13–15 (1995)) and some of these proteins may also require binding to Z-DNA prior to their activity on the double-stranded RNA (Herbert et al., *Proc. Natl. Acad. Sci. USA* 92:7550–7554 (1995)). In addition, other RNA binding proteins, such as AUBF (Malter, *Science* 246:664–666 (1989)) are likely to bind in a structure-independent manner.

Due to the clear importance of RNA/RBP interactions in the regulation of gene expression, these interactions would be an attractive target for drugs that affect them for modulation of protein levels in disease states. To fully exploit these interactions as therapeutic targets, however, requires a clear understanding of how these interactions affect expression, which RBPs are involved in the regulation of RNAs of interest, and the ability to study the modulating effects of potential drugs on the RNA/RBP interactions. To fully exploit such interactions also requires identification of binding sites for RBPs in RNA molecules of interest.

Many investigators have used mobility shift assays to detect RNA/protein interactions. However, the conditions established in one laboratory often fail to detect interactions of different molecules. In addition, the diversity of RNA structures and binding motifs in the protein have led numerous investigators to conclude that a single set of conditions would be impossible to define for detection of multiple different interactions. With more genes being identified as being post-transcriptionally regulated, a universal set of binding conditions would allow for the detection and characterization of the molecules involved in these interactions and ultimately would provide targets for which therapeutics could be developed. Such universal assay conditions have been described in PCT application WO 98/04923.

Therefore, it is an object of the invention to provide an assay for the identification of compounds that affect the interaction of binding sites for RNA binding proteins.

It is a further object of the invention to provide nucleic acid sequences which interact with RNA binding proteins.

SUMMARY OF THE INVENTION

Disclosed are nucleic acid sequences which, when present in an RNA molecule, bind to RNA binding proteins. These nucleic acid sequences are present in untranslated regions of certain mRNA. They can be used in assays to identify compounds that affect the interaction of RNA containing the nucleic acid sequence, such as the source mRNA, and RNA binding proteins. The disclosed nucleic acid sequences can also be used to identify RNA binding proteins that can interact with the sequences.

An assay for identifying compounds that affect interaction of RNA containing one of the disclosed nucleic acid sequences and RNA binding proteins is also disclosed. The assay involves detecting interactions between RNA binding proteins and an RNA molecule containing one of the disclosed nucleic acid sequences in the presence of a test compound and in the absence of the test compound. A difference in the detected interaction in the presence and absence of the test compound indicates that the compound affects the interaction. For example, the assay can be done by forming a test solution and a control solution that each include an RNA molecule containing one of the disclosed nucleic acid sequences, heating the test solution and control solution to denature the RNA molecule, cooling the test solution and the control solution, adding a test compound to the test solution, adding an RNA binding protein to the test solution and the control solution, and detecting interactions between the RNA molecule and the RNA binding protein in the test solution and the control solution. A test compound is identified as a compound having an effect on interactions between the RNA molecule and the RNA binding protein if the interactions detected in the control solution and the interactions detected in the test solution containing the test compound differ.

The identified compounds can be used to affect the interaction of RNA binding proteins with mRNA containing the nucleic acid sequences or related sequences. This can alter expression of the mRNA since a major area of regulation of gene expression involves the regulatory effect of RNA binding proteins interacting with RNA molecules. Interactions between RNA molecules and RNA binding proteins are known to be involved in RNA stabilization, translational efficiency, RNA localization, RNA transcription, RNA editing, and RNA splicing and the identified compounds can be used to affect these processes.

BRIEF DESCRIPTION OF THE DRAWINGS

FIG. 2 is a graph of the amount of radioactively labeled RNA retained on a filter (expressed in percent of the amount of RNA retained on a filter in a reference binding solution) following loading of various binding solutions. All of the binding solutions contained radioactively labeled U1 RNA either alone or including various other components. The first two columns represent binding solutions without RNA binding protein. The remaining columns represent binding solution containing RNA binding protein (K562 extract). WT indicates that the binding solution included the indicated amount of unlabeled wild type RNA as a competitor. MUT indicates that the binding solution included the indicated amount of unlabeled mutant RNA as a competitor. In this instance, the U1 mutant interacts with less affinity than does the wild type sequence.

DETAILED DESCRIPTION OF THE INVENTION

Disclosed are nucleic acid sequences which, when present in an RNA molecule, bind to RNA binding proteins. These nucleic acid sequences are present in untranslated regions of certain mRNA. They can be used in assays to identify compounds that affect the interaction of RNA containing the nucleic acid sequence, such as the source mRNA, and RNA binding proteins. The disclosed nucleic acid sequences can also be used to identify RNA binding proteins that can interact with the sequences.

An assay for identifying compounds that affect interaction of RNA containing one of the disclosed nucleic acid sequences and RNA binding proteins is also disclosed. The assay involves detecting interactions between RNA binding proteins and an RNA molecule containing one of the disclosed nucleic acid sequences in the presence of a test compound and in the absence of the test compound. A difference in the detected interaction in the presence and absence of the test compound indicates that the compound affects the interaction. For example, the assay can be done by forming a test solution and a control solution that each include an RNA molecule containing one of the disclosed nucleic acid sequences, heating the test solution and control solution to denature the RNA molecule, cooling the test solution and the control solution, adding a test compound to the test solution, adding an RNA binding protein to the test solution and the control solution, and detecting interactions between the RNA molecule and the RNA binding protein in the test solution and the control solution. A test compound is identified as a compound having an effect on interactions between the RNA molecule and the RNA binding protein if the interactions detected in the control solution and the interactions detected in the test solution containing the test compound differ.

The identified compounds can be used to affect the interaction of RNA binding proteins with mRNA containing the nucleic acid sequences or related sequences. This can alter expression of the mRNA since a major area of regulation of gene expression involves the regulatory effect of RNA binding proteins interacting with RNA molecules. Interactions between RNA molecules and RNA binding proteins are known to be involved in the following processes, modulation of which has the listed effect on encoded proteins.

RNA-stabilization→protein concentration
RNA destablization→protein concentration
Translational efficiency→protein concentration
RNA localization→protein concentration/function
RNA transcription→protein concentration (viral)
RNA editing→protein function
RNA splicing→protein function

I. Components

A. RNA Binding Proteins

RNA binding proteins for use in the disclosed method can be part of a crude cellular or nuclear extract, partially purified, or extensively purified. RNA binding proteins can be used either in isolation or in combination with one or more other RNA binding proteins. RNA binding proteins can be prepared using known methods for preparing cellular extracts and for purifying proteins. Methods for preparing extracts containing RNA binding proteins and for purifying known RNA binding proteins are described in, for example, Ashley et al., *Science* 262:563–566 (1993), Rouault et al., *Proc. Natl. Acad. Sci. USA* 86:5768–5772 (1989), Neupert et al., *Nucleic Acids Research* 18:51–55 (1990), Zhang et al., *Molecular and Cellular Biology* 13:7652–7665 (1993), and references cited in Burd and Dreyfuss, *Science* 265:615–621 (1994). Individual RNA binding proteins can also be produced recombinantly using known techniques. DNA encoding RNA binding proteins can be obtained from known clones, by synthesizing a DNA molecule encoding an RNA binding protein with a known amino acid sequence, or by cloning the gene encoding the RNA binding protein. Techniques for recombinant expression of proteins and methods for cloning genes encoding known proteins are described by, for example, Sambrook et al., *Molecular Cloning* (Cold Spring Harbor Laboratory, 1989).

Detection of interactions between RNA binding proteins and RNA molecules can be facilitated by attaching a detectable label to the RNA binding protein. Generally, labels known to be useful for proteins can be used to label RNA binding proteins. Preferred labels for RNA binding proteins are $^{125}I$, $^{3}H$, and $^{35}S$. When the RNA binding protein is made recombinantly, it can be labeled by incorporation of labeled amino acids. Techniques for labeling and detecting labeled proteins are well known and are described in, for example, Sambrook et al., and Ausubel et al., *Current Protocols in Molecular Biology* (John Wiley & Sons, Inc., 1996). Detection of RNA binding proteins can also be accomplished with antibodies specific for the RNA binding protein. The production and use of antibodies for this purpose is well known and is described in, for example, Johnstone and Thorpe, *Immunochemistry in Practice* (Blackwell Scientific Publications, 1987).

B. RNA Molecules

RNA molecules containing one of the disclosed sequences can be produced recombinantly using known techniques, by in vitro transcription, and by direct synthesis. For recombinant and in vitro transcription, DNA encoding RNA molecules can be obtained from known clones, by synthesizing a DNA molecule encoding an RNA molecule, or by cloning the gene encoding the RNA molecule. Techniques for in vitro transcription of RNA molecules and methods for cloning genes encoding known RNA molecules are described by, for example, Sambrook et al.

Detection of interactions between RNA binding proteins and RNA molecules can be facilitated by attaching a detectable label to the RNA molecule. Generally, labels known to be useful for nucleic acids can be used to label RNA molecules. Examples of suitable labels include radioactive isotopes such as $^{33}P$, $^{32}P$, and $^{35}S$, fluorescent labels such as fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, and biotin.

Labeled nucleotides are the preferred form of label since they can be directly incorporated into the RNA molecules during synthesis. Examples of detection labels that can be incorporated into amplified RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.* 22:3226–3232 (1994)). A preferred nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into RNA molecules, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

C. Nucleic Acid Sequences Representing RNA Binding Protein Binding Sites

Nucleic acid segments identified as having RNA binding protein binding sites can be used for several purposes. An RNA molecule including the nucleotide sequence of the identified nucleic acid segment can be used in an assay to identify compounds modulating the interaction of the RNA molecule and RNA binding proteins. The identified segment can also be incorporated into a recombinant construct such that expression of the construct is controlled by the nucleic acid segment. For example, an untranslated region of an mRNA identified as interacting with an RNA binding protein can be used as all or a part of the untranslated region of a heterologous RNA. It is expected that such recombinant RNA molecules will interact with the cognate RNA binding protein of the heterologous untranslated region and expression of the RNA will be affected by this interaction. This is analogous to recombining promoters with heterologous coding regions to alter or control the expression of the coding region. It is preferred that recombinant constructs including RNA binding protein binding sites be included in expression vectors such that a recombinant RNA transcript can be produced which includes RBP binding site and heterologous sequences. An identified RBP binding site is said to be operatively linked to heterologous sequences when in an RNA molecule including both binding site and the heterologous sequences, or in a construct in which an RNA transcript can be made including both binding site and the heterologous sequences. As used herein, heterologous sequences are nucleotide sequences that are not naturally associated in the same nucleotide molecule with a reference sequence such as an RBP binding site.

Six nucleic acid segments having RNA binding protein binding sites have been identified and confirmed using procedures described herein. These segments were initially identified as part of biologically important genes in DNA. 5' and 3' UTRs of the gene sequences were identified in databases and amplified from cellular DNA by PCR. Such sequences could also have been cloned using PCR cloning or traditional hybridization cloning out of a library. Once cloned, the UTR is placed under the control of a promoter for in vitro transcription, such as an SP6 or T7 promoter, and radioactively labeled RNA produced. The RNA is then mixed with a protein extract from appropriate cells or an appropriate cell line and binding assessed using the disclosed methods. Specificity of binding is determined by performing the assay in the presence and absence of unlabeled RNA identical to the test RNA (specific competing RNA) and in the presence of unlabeled RNA different from the test RNA (non-specific competing RNA). Once a specific binding site has been identified in a UTR, a more precise localization of the binding site is obtained by standard restriction mapping and re-testing of RNA transcribed from fragments of the UTR.

Each of the segments represent the 3' or 5' untranslated region (UTR) of mammalian mRNA. Three (SEQ ID NO:1, SEQ ID NO:2, SEQ ID NO:3), designated APP-R1, APP-D3, and APP-I1, respectively, are from the 3' UTR of human amyloid precursor protein mRNA (APP). The identified segments are portions of the sequence at GenBank accession number Y00264. Another identified segment (SEQ ID NO:4) is the 3' UTR of human interleukin 10 mRNA (IL10). The identified segment is a portion of the sequence at GenBank accession number M57627. Another identified segment (SEQ ID NO:5) is the 3' UTR of erb-B2 mRNA. The identified segment is a portion of GenBank accession number X03363. Another identified segment (SEQ ID NO:6) is the 5' UTR of human insulin-like growth factor I receptor mRNA (IGF-IR). The identified segment is a portion of GenBank accession number M69229.

Protein extracts for use in the disclosed method can be made generally as follows. Approximately 108 cells can be lysed in buffer containing 25 mM Tris, pH 7.9, 0.5 mM EDTA, 0.1 mM PMSF, 2 mM NaF and 2 mM NaPPi by two cycles of freeze/thawing. Extracts are then centrifuged twice at 16,000×g for 15 minutes at 4° C., aliquoted, snap frozen on dry ice, and stored at −80° C. until use. For APP-R1, APP-D3, and APP-I1 (SEQ ID NO:1, SEQ ID NO:2, SEQ ID NO:3, respectively), SH-SY5Y protein extract was used as a representative cellular extract to demonstrate the presence of a specific regulatory site. For IL10 (SEQ ID NO:4), K562 protein extract was used as a representative cellular extract to demonstrate the presence of a specific regulatory site. For erb-B2 (SEQ ID NO:5), K652 protein extract was used as a representative cellular extract to demonstrate the presence of a specific regulatory site. For IGF-IR (SEQ ID NO:6), protein extract from human pancreatic cell line, LnCAP, Du145, and PC-3 were used as a representative cellular extracts to demonstrate the presence of a specific regulatory site.

One form of an identified RBP binding site is as a nucleic acid molecule that is an RNA molecule, or that can be transcribed into an RNA molecule, where the RNA molecule does not contain a protein encoding nucleotide sequence to which the RBP binding site is naturally linked (that is, linked in nature). That is, in such nucleic acid molecules, the identified RBP binding site has been separated from the protein coding sequence to which it is normally linked. For example, the RBP binding site (SEQ ID NO:6) that has been identified in the 5' untranslated region of IGF-IR mRNA is, in IGF-IR mRNA, naturally linked to a nucleotide sequence encoding IGF-IR. Thus, IGF-IR mRNA is not an RNA molecule that does not contain a protein encoding nucleotide sequence to which the identified human insulin-like growth factor I receptor RBP binding site is naturally linked (even though it includes the RBP binding site) since, in IGF-IR mRNA, the identified IGF-IR RBP binding site is operatively linked to the nucleotide sequence encoding IGF-IR (which is a protein encoding nucleotide sequence to which the nucleotide sequence is naturally linked). The same would be true of any clones of the IGF-IR gene that encode all or a part of IGF-IR.

As used herein, a nucleic acid molecule or nucleic acid segment referred to as having a nucleotide sequence is intended to mean a nucleic acid molecule or segment having the nucleotide base sequence referred to in any of its corresponding forms. For example, in the case of an RNA nucleotide sequence (such as SEQ ID NOs:1–6), it is specifically intended, unless otherwise indicated, that nucleotide molecules or segments referred to as having such an RNA nucleotide sequence include, for example, nucleotide molecules or segments having the corresponding DNA nucleotide sequence (where T is substituted for U). Similarly, in the case of a DNA nucleotide sequence, it is specifically intended, unless otherwise indicated, that nucleotide molecules or segments referred to as having such a DNA nucleotide sequence include, for example, nucleotide molecules or segments having the corresponding RNA nucleotide sequence (where U is substituted for T).

The disclosed nucleic acid sequences can be embodied in RNA by either cloning or direct synthesis, and the RNA can then be used in a screening assay to identify compounds which modulate the interaction of RNA binding proteins with the RNA molecules. Identified compounds can be tested for an effect on expression of a corresponding RNA molecule in a cell. It is preferred that this binding site identification mode be specifically directed to a search of nucleic acid sequences of genes known or suspected of being involved in disease conditions.

D. Assay Conditions for Detecting RNA/RNA Binding Protein Interactions

Interactions between RNA containing one of the disclosed nucleic acid sequences and RNA binding proteins can be detected using any suitable assay. It is preferred that conditions allowing detection of interactions between RNA binding proteins and RNA in general. The disclosed method is facilitated by use of a single set of conditions that allow detection of nearly every interaction of RNA binding proteins and RNA molecules. These conditions allow the formation of detectable complexes between RNA binding proteins and RNA molecules. As used herein, interactions between RNA binding proteins and RNA molecules which are referred to as "possible" are intended to mean those interactions which are specific and which occur under at least one set of conditions (e.g. in vivo or optimized binding assay conditions). These conditions allow detection of a majority of the interactions between RNA binding proteins and RNA molecules which are possible. The meaning of the term "specific interaction" is generally understood to mean interactions that are based on specific characteristics of the interacting molecules and not on general characteristics. For example, certain RNA binding proteins recognize and bind specifically to sites in RNA molecules having the nucleotide sequence AUUUA. This is a specific interaction. Conversely, some proteins bind RNA molecules in general (that is, non-specifically) based on the general chemical characteristics of all RNA molecules. In general, an interaction can be identified as a non-specific interaction by determining that the interaction can be prevented in the presence of a non-specific competitor.

Interactions between RNA binding proteins and RNA molecules are facilitated in a binding solution. The binding solution contains one or more RNA molecules and buffer components. The buffer components include a buffer, a monovalent cation, a divalent cation, a reducing agent, and a density agent. It is preferred that the buffer is Bis-Tris Propane at a pH of about 8.5 and at a concentration of about 7.5 mM, the monovalent cation is $K^+$ at a concentration of about 50 mM, the divalent cation is $Mg^{++}$ at a concentration of about 1 mM, the reducing agent is dithiothreitol at a concentration of about 0.2 mM, and the density agent is glycerol at a concentration of about 10 percent (v/v).

These conditions have been optimized to be universally applicable. It is most preferred that the optimum conditions be used. However, one, or less preferably two, of the buffer components can be varied in the manner disclosed below. For varying certain buffer components, it is preferred that (1) the buffer is HEPES, Tris, or Bis-Tris Propane, each at a pH between about 8 and 10 and at a concentration of between about 5 and about 100 mM, (2) the monovalent cation is $K^+$, $Na^+$, or $NH_4^+$, each at a concentration of between 0 and about 100 mM, (3) the divalent cation is $Mg^{++}$, $Ca^{++}$, or $Fe^{++}$, each at a concentration of between 0 and about 5 mM, (4) the reducing agent is dithiothreitol or β-mercaptoethanol, at a concentration of between 0 and about 1 mM, and the density agent is glycerol or polyethylene glycol at a concentration of between 0 and about 20 percent (v/v).

For most RNA molecules, the reducing agent does not appear to be critical, although there is a trend to slightly better binding in the presence of a reducing agent, preferably DTT. However, in some cases the reducing agent makes a significant difference in the detection of interactions. Accordingly, the use of a reducing agent is preferred. A density agent does not appear to be required for detecting the interaction between RNA molecules and RNA binding proteins. However, when interactions are analyzed by gel mobility shift, the presence of a density agent does enhance the quality of the bands. Accordingly, the use of a density agent is preferred.

The binding solution can include other components that aid in the formation of specific interactions. For example, a competitor of non-specific RNA/protein interactions can be added to reduce the background of non-specific interactions. Poly r(G), tRNA, and heparin, are preferred competitors of non-specific RNA/protein interactions.

It is intended that a concentration range stated as between 0 and about a specific concentration does not encompass a concentration of zero but does encompass the specific concentration and concentrations up to about 10% greater than the specific concentration. It is also intended that a concentration range stated as between about a first specific concentration and about a second specific concentration encompasses the first specific concentration, concentrations up to about 10% lower than the first specific concentration, concentrations between the first and second specific concentrations, the second specific concentration, and concentrations up to about 10% greater than the second specific concentration. It is intended that a concentration range stated as from a first specific concentration to a second specific concentration encompasses the first specific concentration, concentrations between the first and second specific concentrations, and the second specific concentration. It is also intended that a concentration range stated as from 0 to a specific concentration encompasses a concentration of zero, concentrations between zero and the specific concentration, and the specific concentration.

Unless otherwise noted, all concentrations of buffer components are intended to be the final concentration of these components in a completely formed binding solution. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA.

It is preferred that the concentration of extraneous compounds be kept to a minimum in binding solutions. It is understood, however, that samples of RNA binding proteins and RNA molecules may contain additional compounds. The concentration in the binding solution of such compounds can be reduced by, for example, diluting the sample to the greatest extent possible when forming the binding solution.

II. Method

The basic method for identifying compounds that affect RNA/RNA binding protein interactions involves detecting such interactions in the presence and the absence of a test compound.

A. Detection Of RNA/RBP Interactions

Detection of an interaction between an RNA binding protein and a putative binding site can be performed using assays as disclosed. Such assays can also be used to screen for compounds that affect the interaction between RNA and RNA binding proteins. The basic method for detecting interactions between RNA molecules and RNA binding proteins involves forming a binding solution containing the RNA molecules and 1×binding buffer, heating the binding solution to denature the RNA molecules, cooling the binding solution to the reaction temperature, adding the RNA binding proteins to the binding solution, and detecting the interactions between the RNA molecules and the RNA binding proteins. Compounds to be tested for their effect on RNA/RNA binding protein interactions can be added at any stage of the assay. For example, the compound can be added prior to or with the RNA, prior to or with the RNA binding protein, or after adding the RNA binding protein.

1. Forming the Binding Solution

The binding solution contains one or more RNA molecules, buffer components, and non-specific competitors. The buffer components include a buffer, a monovalent cation, a divalent cation, a reducing agent, and a density agent. The binding solution is formed by combining and/or mixing together the constituents of the binding solution in any manner that results in a binding solution having the required composition. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA. Thus, the manner in which the final composition of the binding solution is arrived at is not critical. It is intended that any combination of solutions and components that achieves this result is encompassed by this step.

2. Heating and Cooling the Binding Solution

The formed binding solution is heated and cooled in 1×binding buffer in order to denature any higher order structure in the RNA molecules. Such structures can make the RNA molecules less accessible to the RNA binding proteins. When using RNA molecules purified from natural sources, it is also possible that other molecules can remain bound to the RNA. The heating step can serve to release such molecules. The heating and cooling step involves subjecting the binding solution to a heat source until it reaches a sufficient temperature, and then allowing the solution to cool to the reaction temperature. The temperature to which the binding solution is heated can be any temperature that will substantially denature the RNA molecules present in the binding solution. It is understood that different temperatures will be sufficient for different RNA molecules. For example, shorter RNA molecules and RNA molecules with a low GC content will, in general, be substantially denatured at lower temperatures. However, it is preferred that a single temperature be used for the heating step. In this case, it is preferred that a temperature sufficient to substantially denature RNA molecules in general be used. A preferred temperature is 85° C. After allowing the solution to cool to the reaction temperature, the RNA binding protein is added to the binding solution prior to incubation at the appropriate temperature for RNA-protein binding, preferably 37° C.

3. Detecting Interactions

Interactions between RNA binding proteins and RNA molecules can be detected using any suitable procedure. It is preferred that detection involve separation of interacting RNA molecules and RNA binding proteins. This can be accomplished, for example, by separating components in the binding solution on the basis of size or physical properties. Two preferred methods of separation and detection of interacting RNA molecules and RNA binding proteins are filter binding and gel mobility shift.

a. Filter binding. Filter binding involves trapping interacting molecules on a filter while non interacting molecules pass through the filter. This procedure is known to those of skill in the art. For example, prewet nitrocellulose filters are equilibrated in 1×binding buffer. The binding reaction is then applied to the filter by vacuum filtration to remove unbound RNA. The filter is washed in 1×binding buffer, scintillation cocktail is added and the amount of protein-bound RNA is determined by scintillation counting.

For assays involving filter binding, it is also preferred that a non-interacting control assay be performed. Such a control is used to determine the detectable signal retained in the absence of specific RNA/RNA binding protein interaction. Preferably, such a non-interacting control assay is performed by substituting a mutant RNA molecule—one that does not interact specifically with the RNA binding protein—for the RNA molecule used in corresponding binding assays. The level of detectable signal bound to the filter in the non-interacting control indicates the contribution of background, or non-specific, signal present in the level of detectable signal measured for the binding assays. In the high throughput screening assay, the non-interacting control is also a control for the control assays (that is, assays not containing a test compound). It is expected that the level of background signal can be reduced by including a low concentration of detergent in the wash buffer. Preferred detergents for this purpose are Tween 20 and Triton N-101. For a given set of test reactions, a non-interacting control assay can be used to determine the effectiveness of the washes.

It is preferred that the concentration of RNA binding protein in the disclosed assays be at least 0.5 μg/μl or between 0.5 μg/μl and 1.0 μg/μl. For assays using filter binding, the filter is preferably either pure nitrocellulose or a mixed cellulose ester (MCA). For the disclosed assay, the mixed cellulose ester filters bound more counts than pure nitrocellulose. For the filters, a 0.2 μm pore size (8000 dalton MW cutoff) is most preferred, although MCA filter plates with a 0.45 μm pore size (20,000 dalton MW cutoff) are also preferred. The lower molecular weight cutoff allows detection of binding interactions between RNA and small molecular weight proteins. For the high throughput screening assay, it is preferred that the binding reactions are carried out in 96 well v-bottom plates in a final volume of 10 μl. For this, the samples are loaded onto a 96 well Millipore filter plate.

For assays using filter binding, it is preferred that, following incubation and prior to loading unto the filter, the reactions be brought to a larger final volume, most preferably a final volume of 110 μl, by the addition of a solution, referred to as the dilution solution. Preferred dilution solutions include 1×Bis-Tris propane (BTP) binding buffer with glycerol, 1×BTP without glycerol, TE, phosphate buffered saline (PBS), and trichloroacetic acid (TCA), with 1×BTP without glycerol being most preferred. It is most preferred that the dilution solution have the same buffer components (preferably at the same final concentration) as used in the binding solution except lacking the density agent. This dilution allows more even loading of the sample on the filter plate. It is contemplated that the preferred final volume used should differ depending on the area of filter to which the assay solution will be applied. Thus, assays in which larger filter areas are used are preferably brought to a final volume greater than 110 μl and assays in which smaller filter areas are used are preferably brought to a final volume less than 110 μl.

It is preferred that the assay solution be loaded onto the filter under vacuum. After loading, it is preferred that the filters be washed, preferably two times. Preferred wash buffers (also referred to as the wash solution) include 1×BTP binding buffer with glycerol, 1×BTP without glycerol, TE, PBS, and TCA, with 1×BTP without glycerol being most preferred. It is most preferred that the wash buffer have the same buffer components (preferably at the same final concentration) as used in the binding solution except lacking the density agent. It is also preferred that the wash buffer be cold (that is, below room temperature).

b. Gel mobility shift. Gel mobility shift involves resolving interacting and non-interacting RNA molecules and RNA binding proteins on a gel by electrophoresis and visualizing the location and amount of components that migrate to different extents. Interacting RNA molecules and RNA binding proteins tend to migrate less in the gel than non-interacting molecules by virtue of their greater mass. Gel mobility shift assays can be performed as follows. After incubation of the binding reaction, 6×loading buffer (30% glycerol, 0.25% xylene cyanol, 0.25% bromophenol blue) is added to a final concentration of 1×. The reaction is then loaded into the wells of a polyacrylamide gel (generally 4 to 8%) prepared in Tris-borate EDTA (TBE) buffer (90 mM Tris-borate, 2 mM EDTA, pH 8). The protein-bound RNA is separated from the unbound RNA by applying a constant voltage (150 to 175 V) to the gel and allowing the gel to run until the bromophenol blue has reached the bottom of the gel. The gel is the dried in vacuo at 80° C. The unbound RNA and the protein-bound RNA are then visualized autoradiographically. In cases where it is desirable to know the molecular weight of the RNA-protein complex, the binding reaction is subjected to ultraviolet light to covalently crosslink the complex. 6×loading buffer (3.75 M Tris, 30%

βME, 13.8% sodium dodecyl sulfate (SDS), 30% glycerol, pH 6.8) is added to the crosslinked reaction at a final concentration of 1× and the mixture is loaded onto a SDS-polyacrylamide gel (generally 8 to 12%). The gel is run in a Tris-glycine buffer (25 mM Tris, 192 mM glycine, 0.1% SDS) at 30 mA until the molecular weight markers are adequately separated. The gel is dried and the RNA-protein complex visualized autoradiographically.

c. Ribonuclease digestion. For some assays it may be desirable to eliminate those RNA molecules, or those regions of an RNA molecule, that are not involved in an interaction with RNA binding proteins. For example, when a large RNA molecule is used in the assay, binding of an RNA binding protein might result in an RNA/protein complex only slightly larger than the RNA molecule alone. When detecting such a complex by gel mobility shift, the resulting shift may not be easily detectable. When detecting such a complex by filter binding, the RNA molecule alone may be sufficiently large to be retained by the filter. Such potential problems can be mitigated by digesting RNA not involved in interactions. This is easily accomplished by subjecting the binding solution to ribonuclease digestion. Only the unbound or non-interacting RNA will be digested. The regions of RNA bound by RNA binding proteins will be protected from digestion by the protein.

B. Screening For Compounds That Modulate Interaction Of RNA Molecules And RNA Binding Proteins Identification of compounds that modulate the interaction of RNA molecules and RNA binding proteins can be accomplished by including one or more test compounds in the binding solution comprising the RNA molecules of interest, the RNA binding proteins of interest, and buffer components, and detecting the interaction between the RNA molecules and the RNA binding proteins. Test compounds that modulate or affect the interaction between the RNA molecules and RNA binding proteins can be identified by comparing the interactions in the binding solution that does not contain the test compound with the interactions in the binding solution containing the test compounds. Binding solutions that include one or more test compounds are referred to herein as test solutions. Binding solutions that do not include a test compound are referred to herein as control solutions. Compounds that modulate the interaction will be identified if the interactions in the two solutions differ. An assay of this type can be used to identify compounds that modulate or affect the interaction by binding to the RNA molecules or by binding to the RNA binding proteins in a given sample. By delivering an identified compound to a cell in which an RNA molecule of interest, or a related RNA molecule, is expressed, the function or action of the RNA molecule in the cell can be affected due to the modulation or effect the compound has on the interaction of the RNA molecule and RNA binding proteins. For example, where an interaction between a mRNA molecule and an RNA binding protein controls the translation of the mRNA, a compound identified as affecting that interaction in the disclosed assay can be used to affect the translation of the mRNA via its effect on the interaction. Identified compounds can be used to affect the function or expression of an RNA molecule in a cell in vivo, ex vivo, or in vitro. The identification of such compounds can also lead to the development of therapies to treat a variety of diseases. Such compounds can also be used as research tools to study the significance, nature, or mechanism of RNA function or expression in a cell.

a. High throughput screening assay. Although not required, The disclosed universal assay conditions can be used in a screening assay to identify compounds which affect a RNA/RNA binding protein interaction of interest. Such screening assays can be designed to allow simultaneous assessment of the effect of numerous test compounds on the interaction of interest. For this purpose, it is preferred that the interactions be detected by filter binding. Simultaneous filter binding assays are preferably performed by simultaneous filtering of binding solutions in an apparatus having separate wells, holes, slots, or other compartments which can hold separate binding solutions. A preferred form of multi-well filter binding apparatus is the MultiScreen filter plate of Millipore. It is also contemplated that multiple multi-well or multi-sample assays can be performed simultaneously.

In general, high throughput screening can be performed as follows. First, a set of one or more test solutions is formed, where each test solution includes one or more RNA molecules and buffer components. The test solutions are then heated for a time and to a temperature sufficient to denature the RNA molecule(s), and slowly cooled. Next, one or more RNA binding proteins are added to the test solutions, and interactions between the RNA molecule(s) and the RNA binding protein(s) in the test solutions are detected. One of the test compounds is included in the test solution. To determine whether the test compounds have an effect on the interactions between the RNA molecule(s) and the RNA binding protein(s) a control solution is formed, heated, and cooled as with the test solutions, except that no test compound is present in the control solution. The RNA binding protein(s) are added to the control solution, and interactions between the RNA molecule(s) and the RNA binding protein (s) in the control solution are detected. By comparing the interactions detected in the test solutions with those detected in the control solution, it can be determined if a given test compound has an effect on the interactions. A test compound is identified as a compound having an effect on interactions between the RNA molecule(s) and the RNA binding protein (s) if the interactions detected in the control solution and the interactions detected in the test solution containing the test compound differ.

The test compound can be added to the test solution at any time, for example, during formation of the test solution, prior to the heating step, prior to adding the RNA binding protein, or with the RNA binding protein. It is preferred that the test compound is mixed with either the RNA molecule or the RNA binding protein prior to their addition to the test solution.

The assay using the control solution can be performed separately from, or together with, the assays of the test solutions. When performed separately, the control solution assay can be performed either before, after, or simultaneous with the test solution assays. It is preferred that the control solution assay be performed together and simultaneous with the test solution assays.

As used herein a set of test solutions refers to one or more test solutions which are related to each other by having the same RNA binding protein(s), RNA molecule(s), and buffer components. The test solutions within a set of test solutions preferably differ from each other in the test compound present in the test solution. It is contemplated and preferred that a single control solution, or a single form of control solution, be used for comparison of interactions detected in an entire set of test solutions. For this purpose it is preferred that the control solution have the same RNA binding protein (s), RNA molecule(s), and buffer components as the test solutions in the set. Multiple sets of test solutions, and a control solution for each set, can also be assayed together in a high throughput assay. For this purpose it is preferred that either or both of the RNA binding protein(s) or the RNA molecule(s) differ between each set of test solutions. For assays involving such multiple sets of test solutions, it is preferred that each set of test solutions use the same set of test compounds.

Preferred relationships between test solutions, sets of test solutions, and control solutions, as described above, can be illustrated with the following schematic examples. In the following examples, different RNA molecules or sets of RNA molecules (a given solution can contain a single RNA molecule or multiple RNA molecules) are referred to R1, R2, R3, etc. Different RNA binding proteins are referred to as P1, P2, P3, etc. Test compounds are referred to as C1, C2, C3, etc. Buffer components, as a group of components in a given solution, are referred to as B1, B2, B3, etc.

Three sets of test solutions, referred to as set 1, set 2, and set 3, are set up using the following components:

|  | Set 1 | Set 2 | Set 3 |
|---|---|---|---|
| RNA | R1 | R2 | R3 |
| Protein | P1 | P2 | P3 |
| Buffer | B1 | B1 | B1 |

For each set, a different control solution is set up using these same components. Thus, each set is designed to assess the effect of test compounds on a different RNA/RNA binding protein interaction (or group of interactions). A different test compound can be included in each test solution in each set as follows:

| Test solution | Set 1 | Set 2 | Set 3 |
|---|---|---|---|
| 1 | C1 | C1 | C1 |
| 2 | C2 | C2 | C2 |
| 3 | C3 | C3 | C3 |
| 4 | C4 | C4 | C4 |
| .... | .... | .... | .... |
| 92 | C92 | C92 | C92 |
| 93 | C93 | C93 | C93 |
| 94 | C94 | C94 | C94 |
| 95 | C95 | C95 | C95 |

No test compound is added to the control solutions. As can be seen, in this example, the same bank of 95 test compounds are tested for an effect on each of the three RNA/RNA binding protein interactions. Similar groups of assays could be performed using a different set of test compounds, or a partially overlapping set of compounds. The entire group of assays described above can be performed simultaneously and, preferably, is automated. The number of assays in any set of test assays can be increased to accommodate as many test compounds as desired. In such cases, of course, it is preferred that the set of test assays be divided into manageable groups, based on, for example, the number of wells in a multi-well filter apparatus. It is contemplated that the disclosed method can be performed using devices and apparatus designed to accommodate a large number of test assays.

b. Preferred modes of identifying compounds. It is preferred that interactions be detected in an automated manner using, for example, automated detection and comparison of interaction signals. Where the RNA molecule(s) or the RNA binding protein(s) are labeled with a detectable group, it is preferred that interactions be detected using automated quantitative detectable group. For this purpose, it is preferred that the detectable group include a component that produces, either directly or indirectly, a quantifiable signal. Preferred components of this type are radioactive isotopes. Reagents and methods for the use and detection of radioactive labels are well known.

Simultaneous gel shift assays are preferably accomplished by subjecting multiple binding solutions to electrophoresis in a single gel with multiple lanes, and in multiple gels each with multiple lanes. Detection and comparison of multiple samples can be accomplished by, for example automated detection and localization of interacting complexes in the gel lanes.

It is preferred that the test compounds be mixed with either the RNA molecule, either before, during or after formation of the binding solution, or the RNA binding protein prior to addition to the binding solution. For this purpose, it is preferred that the test compound be mixed with either the RNA molecule or the RNA binding protein depending on with which of these components it is desired or expected the test compound will interact. For example, if compounds affecting the interaction of an RNA and an RNA binding protein via interaction with the RNA are desired (or expected, given the nature of the test compounds), then the test compound should be added to the RNA. Conversely, if compounds affecting the interaction of an RNA and an RNA binding protein via interaction with the RNA binding protein are desired (or expected, given the nature of the test compounds), then the test compound should be added to the RNA binding protein. It is most preferred that the test compound be added to the binding solution after heating and cooling and before addition of the RNA binding protein. It is also preferred that all of the test solutions in a given set of test solutions have the test compound mixed in the same way and at the same stage for all of the assays.

c. Identified compounds. Compounds identified as having an effect on interactions between RNA molecules and RNA binding proteins can be used to affect such interactions in cells. In the case where the interaction between an RNA molecule and an RNA binding protein affects the function or expression of the RNA molecule, a compound having an effect on the interaction is expected to have an effect on the function or expression of the RNA molecule. Thus, it is contemplated that compounds identified having an effect on the interaction of an RNA molecule and an RNA binding protein will be useful for affecting the function or expression of the RNA molecule in a cell. Such compounds can be delivered to cells in any manner which allows the compound to have the desired effect. Many such modes of delivery are known in the art. A preferred form of delivery for in vivo applications are compositions combining an identified compound and a pharmaceutically acceptable carrier. For this purpose, the disclosed method can include a step of forming such a composition. For in vitro and ex vivo applications, an identified compound can be added to the culture medium. The compound can also be combined with any delivery system or composition that can enhance the entry of the compound into the cell and/or enhance the delivery of the compound to particular cells.

Suitable pharmaceutical vehicles for administration to a patient are known to those skilled in the art. For parenteral administration, the compound can be dissolved or suspended in sterile water or saline. For enteral administration, the compound can be incorporated into an inert carrier in tablet, liquid, or capsular form. Suitable carriers may be starches or sugars and include lubricants, flavorings, binders, and other materials of the same nature. The compound can also be administered locally at a desired site by topical application of a solution or cream.

Alternatively, the compound may be administered in, on or as part of, liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14 in "Liposomes", pages 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The criteria for assessing response to therapeutic modalities employing an identified compound is dictated by the specific condition and will generally follow standard medical practices. Generally, the effect of administration of a compound can be assessed at least by determining if the RNA/RNA binding protein interaction determined to be affected by the compound is in fact affected in cells to which the compound is administered or delivered. Such an assessment can also be made by determining if there is an effect on a surrogate for the interaction, such as expression of an RNA, production of a protein, or a consequent physiological effect. Where the RNA/RNA binding protein interaction affected by the protein is known or suspected to involve the function or expression of an RNA involved in a disease condition, the effectiveness of administration of the compound can be assessed by measuring changes in characteristics of the disease condition.

C. Identifying RNA Molecules and RNA Binding Molecules That Interact With Specific RNA Binding Proteins and RNA Molecules Identification of RNA molecules that interact with a specific RNA binding protein can be accomplished by forming a binding solution comprising one or more RNA molecules, and buffer components comprising a buffer, a monovalent cation, a divalent cation, a reducing agent, and a density agent, adding the specific RNA binding protein, and detecting interactions between the one or more RNA molecules and the RNA binding protein. Those RNA molecules that interact can be identified by specific sequence analysis. This is how the disclosed RNA binding protein binding sites were identified. An assay of this type can be used to identify all those RNA molecules in a given sample which are specific for an RNA binding protein of interest. The identification of such RNA molecules can lead to the identification of genes encoding RNA molecules regulated by the RNA binding molecules of interest.

In a similar way, RNA binding proteins that interact with a specific RNA molecule can be identified by forming a binding solution comprising the RNA molecule of interest, and the buffer components, adding one or more RNA binding proteins, and detecting interactions between the one or more RNA binding proteins and the RNA molecule.

D. Identifying Regions In RNA Molecules That Interact With RNA Binding Proteins

Regions in RNA molecules that interact with RNA binding proteins can be identified by forming a binding solution comprising (1) an RNA molecule from a subset of RNA molecules consisting of successively smaller fragments of a larger RNA molecule previously identified to be involved in an RNA-protein interaction, or (2) an RNA molecule containing one or more mutations or deletions in a previously identified RNA molecule involved in an RNA-protein interaction, buffer components comprising a buffer, a monovalent cation, a divalent cation, a reducing agent, and a density agent, and non-specific competitors, adding one or more RNA binding proteins, and detecting the interaction between the RNA molecule and the RNA binding proteins. By comparing which RNA molecules interact with the binding proteins to those which do not interact, the region of the RNA molecule involved in the interaction can be identified. An assay of this type can identify all the regions in an RNA molecule involved in an interaction with an RNA binding protein as well as identifying the specific nucleotides that interact with the RNA binding protein. This assay can be used with the disclosed sequences to refine or identify the binding sites.

EXAMPLES

Example 1

Assays Using Universal Conditions

Several assays for detecting interactions between RNA molecules and RNA binding proteins were performed by (1) forming a binding solution including RNA molecules, BTP at pH 8.5, 50 mM KCl, 1 mM $MgCl_2$, 0.2 mM DTT, and 10% glycerol, (2) heating the binding solution to denature the RNA molecules, (3) cooling the binding solution, (4) adding RNA binding proteins to the binding solution, and (5) detecting the interactions between the RNA molecules and the RNA binding proteins. In the first assay, interactions of several RNA molecules (radioactively labeled) with different recognition features were incubated with SH-SY5Y or CHL/260 protein extract. The SH-SY5Y extract was prepared as follows. Approximately 108 SH-SY5Y cells were lysed in buffer containing 25 mM Tris, pH 7.9, 0.5 mM EDTA, 0.1 mM PMSF, 2 mM NaF and 2 mM NaPPi by two cycles of freeze/thawing. Extracts were centrifuged twice at 16,000×g for 15 minutes at 4° C., aliquoted, snap frozen on dry ice, and stored at −80° C. until use. The RNA molecules were chosen to highlight detection of interactions dependent on RNA sequence (AUUUA RNA), sequence and RNA structure (histone RNA), or RNA structure alone (double-stranded RNA). AUUUA RNA has the sequence AUUUAU-UUAUUUAUUUAUUUA (SEQ ID NO:8). Double stranded RNA has the sequence GGAGCGUACGCGAGC UACAGGCUCGCGUACGCUCC (SEQ ID NO:9). In addition to these small RNA molecules (less than 30 nucleotides), the 210 nucleotide 5' untranslated region of glucose transporter type 1 (Glut1) was also tested (SEQ ID NO:7). SH-SY5Y protein extract was used with AUUUA RNA and CHL/260 protein extract was used with the remaining RNA molecules. The gel contained multiple slower migrating bands in each of the lanes. This indicates that the universal assay conditions allow detection of interactions between RNA molecules and RNA binding proteins across the spectrum of interaction types.

In another assay, interactions of several RNA molecules representing targets for different binding motifs were incubated with SH-SY5Y or CHL/260 protein extract or recombinant Rev protein. The RNA molecules were chosen to highlight detection of interactions involving RNA binding proteins containing double-stranded RNA binding motifs (IRE-BF; *Proc. Natl. Acad. Sci. USA* 86:5768–5772 (1989)), RGG box (APP-BF; *J. Biological Chem.* 270:17292–17298

(1995)), Arg-rich motifs (RRE-BF; *Biochemistry* 33:14579–14585 (1994)), and RNP motifs (U1-BF; *J. Mol. Biol.* 180:947–960 (1984)). SH-SY5Y protein extract was used in the APP-BF assay, CHL/260 protein extract was used with the IRE-BF and U1-BF assays, and recombinant Rev protein was used with the RRE-BF assay. The gel contained multiple slower migrating bands in each of the lanes. This indicates that the universal assay conditions allow detection of interactions between RNA molecules and RNA binding proteins across the spectrum of interaction types.

In another assay, the specificity of the interaction being detected was confirmed. Radioactively labeled IRE RNA was incubated in the presence or absence of K562 protein extract. K562 was prepared as described above. To test whether interactions detected were specific or not, unlabeled IRE was also included in some of the assays. This RNA competes with the labeled IRE RNA for interaction with RNA binding proteins. As a control, unlabeled mutant IRE (which is defective for binding) was included in some assays. If the interaction is specific, this RNA should not compete with the labeled IRE RNA for the RNA binding proteins. In gel lanes for assays where no protein extract was included, no mobility shift is visible, as expected. In gel lanes for assays where protein extract was included, a clear mobility shift is visible. In assays where increasing concentrations (100×, 1,000×, and 10,000×, respectively) of unlabeled IRE RNA was included, the unlabeled RNA effectively competes with the labeled RNA for interaction with the RNA binding proteins at the 1,000×, and 10,000× concentrations. In assays where increasing concentrations (100×, 1,000×, and 10,000×, respectively) of mutant IRE RNA was included, the unlabeled RNA is unable to compete with the labeled RNA for interaction with the RNA binding proteins. This clearly indicates that the competitive effect of unlabeled IRE RNA is not due to non-specific interactions between the RNA molecules and the RNA binding proteins.

Example 2

High-Throughput Screening Assay

The following assays demonstrate modes and the effectiveness of the disclosed high throughput screening assay. All binding reactions were performed in 96-well v-bottom plates in a final volume of 10 μl. The assays were constituted and performed as described below. Specifically, assays were performed by (1) forming a binding solution including RNA molecules, 7.5 mM BTP at pH 8.5, 10 mM KCl, 5 mM $MgCl_2$, 0.2 mM DTT, and 10% glycerol, (2) heating the binding solution to denature the RNA molecules, (3) cooling the binding solution, (4) adding RNA binding proteins to the binding solution, (5) loading the binding solution onto a filter, and (6) detecting the amount RNA retain on the filter.

The nitrocellulose filter plate was precoated with bovine serum albumin (BSA), polyvinylpyrrolidone (PVP), polyG, polyI, polyc, polyu or tRNA as a blocking agent prior to loading the assay solutions. Regardless of whether the well was untreated or precoated with a blocking agent, the free RNA cpms (that is, RNA retained on the filter in the absence of RNA binding protein measured in radioactive counts per minute (cpm)) were 7 to 12% of the protein-bound cpms. This indicates that blocking is not required or preferred.

Competition Assays

Figure 1:
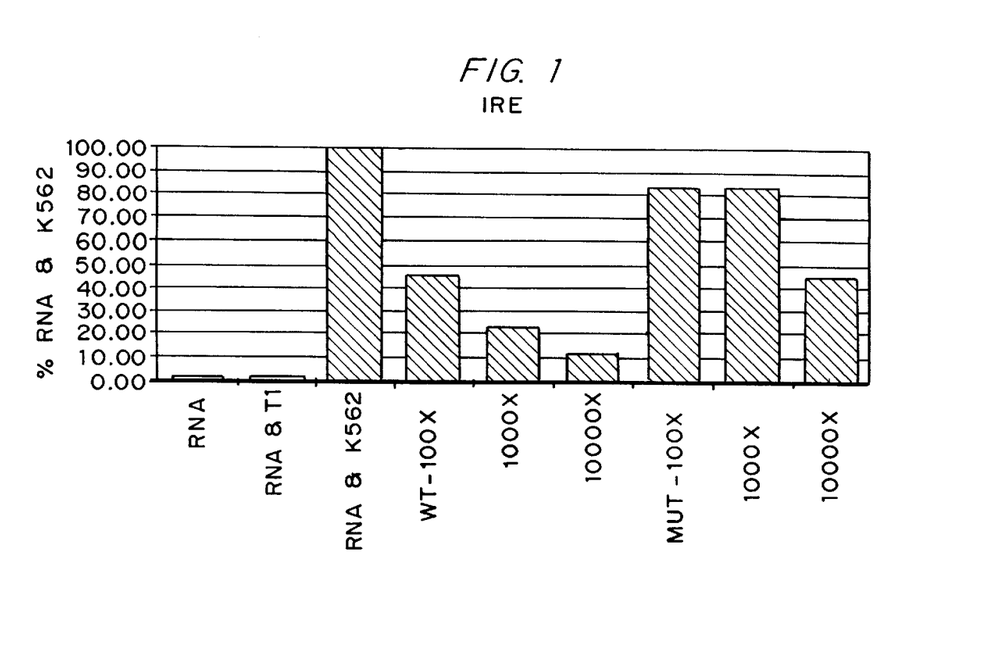
FIG. 1 is a graph of the amount of radioactively labeled RNA (in counts per minute) retained on a filter following loading of various binding solutions. All of the binding solutions contained radioactively labeled APP RNA either alone or including various other components. T1 indicates that the binding solution was treated with RNAse T1 prior to loading. The first two columns represent binding solutions without RNA binding protein. The remaining columns represent binding solution containing RNA binding protein. WT indicates that the binding solution included the indicated amount of unlabeled wild type RNA as a competitor. MUT indicates that the binding solution included the indicated amount of unlabeled mutant RNA as a competitor.

To test the ability of the filter assay to detect changes in binding activity (that is, decreased interaction between RNA and RNA binding proteins) competition assays were performed with IRE RNA and K562 protein extract (see FIG. 1). Competition experiments were performed by adding increasing concentrations (100 to 10,000×) of unlabeled wild-type or mutant IRE RNA to the binding reaction. FIG. 1 illustrates the results. A concentration dependent inhibition of binding was observed in assays in which the unlabeled wild-type RNA was added whereas no competition was observed in assays in which unlabeled mutant RNA was added.

Figure 2:
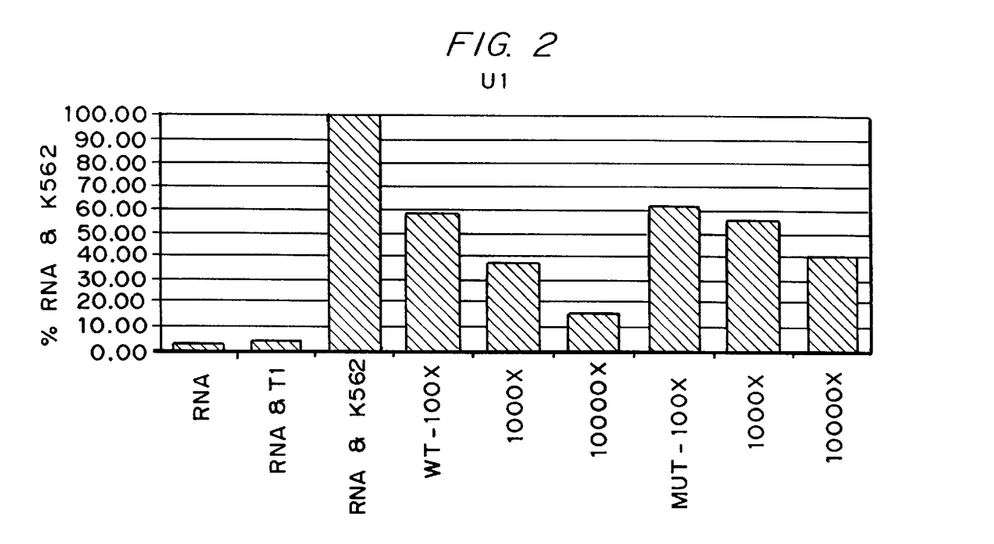

To more fully test the filter assay, competitions were performed with U1 and His RNAs as well. U1 RNA has the sequence AAUCCAUUGCAC UCCGGAUUU (SEQ ID NO:10; M14587). His RNA has the sequence AAAAAG-GCUCUUUUCAGAGCCACCCA (SEQ ID NO:11; X57138). Both U1 and His wild-type RNAs showed a concentration dependent inhibition of binding (see FIG. 2). However, the mutant RNAs also inhibited binding in a concentration dependent manner, although at about 10-fold higher concentration. FIG. 2 illustrates these results for the U1 competition. In these competition assays, unlike the IRE assay, the mutant RNA used has been shown to bind the RNA binding protein, although with a lower affinity than the wild-type RNA. The results of the U1 and His filter assay competitions reflect the ability of the assay to detect low affinity as well as higher affinity binding interactions.

Modulation of the Binding Interaction by Small Molecules

Figure 3:
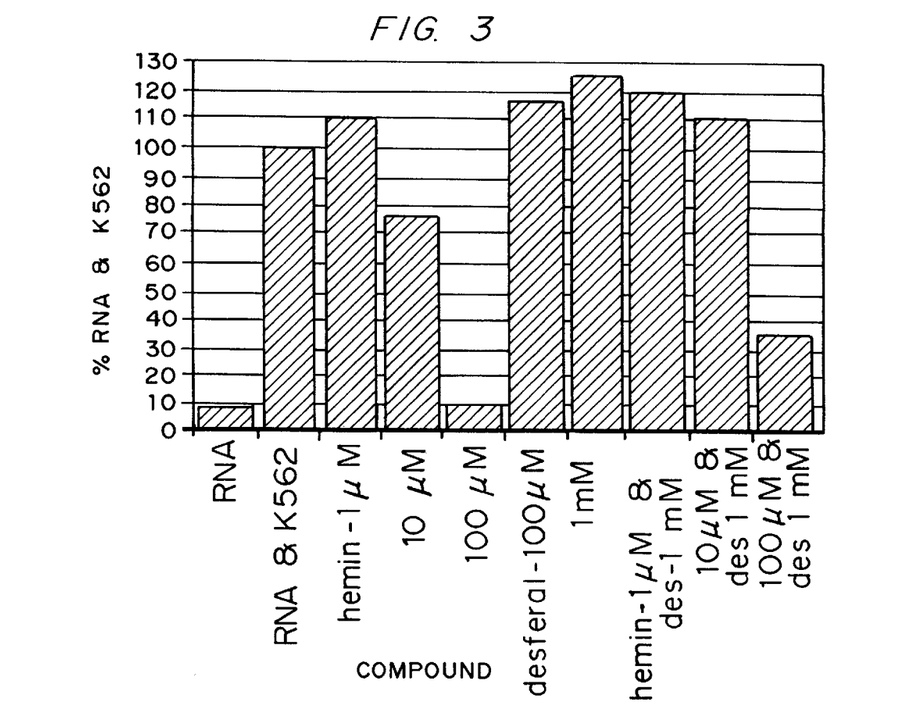
FIG. 3 is a graph of the amount of radioactively labeled RNA retained on a filter (expressed in percent of the amount of RNA retained on a filter in a reference binding solution) following loading of various binding solutions. All of the binding solutions contained radioactively labeled IRE RNA either alone or including various other components. The first column represents a binding solution without RNA binding protein. The remaining columns represent binding solution containing RNA binding protein (K562 extract). Hemin indicates that the binding solution included the indicated amount of hemin as a test compound. Des indicates that the binding solution included the indicated amount of desferroxiamine as a test compound.

Binding assays were performed with wild-type IRE RNA and K562 protein extract in the presence of sources of iron or iron chelators to determine the ability of the filter assay to detect the modulation of binding interactions by small molecules. Increasing concentrations of the iron sources hemin (1 to 100 μM) and $FeCl_3$ (1 μM to 1 mM) or the iron chelator desferroxiamine (1 μM to 1 mM) were added to the binding reactions (see FIG. 3). Hemin and $FeCl_3$ produced a concentration-dependent inhibition of binding. Desferroxiamine did not change the amount IRE/protein complex formed, perhaps because there is not enough iron in the cell extract to produce a noticeable change upon addition of desferroxiamine. The reactions were analyzed by gel shifts to visualize the results of the filter assay.

Exploratory Library Screen

A 96 member exploratory compound library that contained CNI-1493, a compound previously shown to post-transcriptionally inhibit TNF-α production, was generated. The library was initially screened at 10 μM against $^{32}$P-labeled AUUUA RNA. Several methods of introducing the compounds into the binding reaction were tested. Initially the compounds were co-incubated with the RNA and protein, producing modest results. Next, preincubation with either the protein extract or the RNA was tried with improved results.

Figure 4:
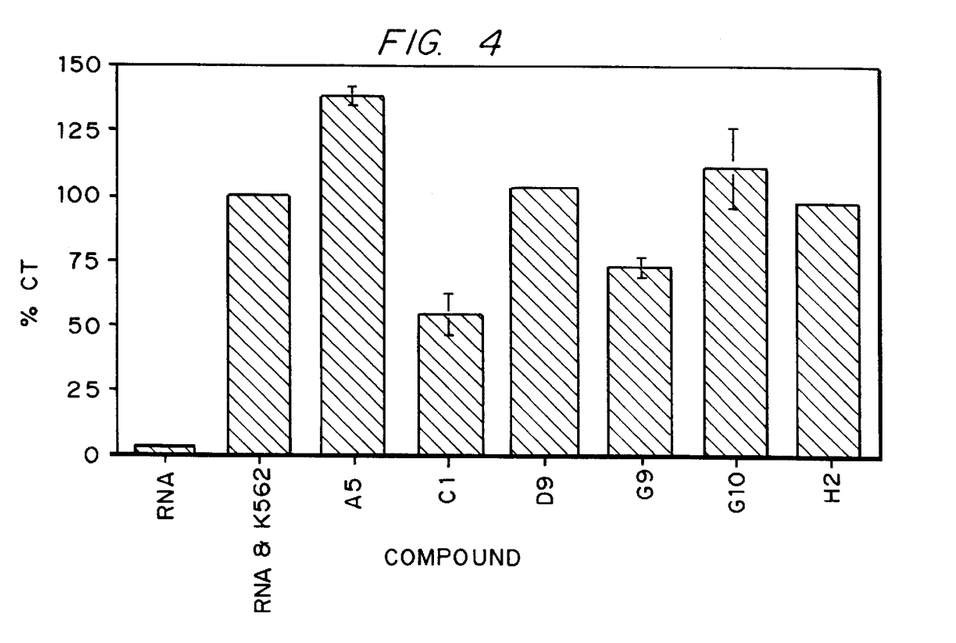
FIG. 4 is a graph of the amount of radioactively labeled RNA retained on a filter (expressed in percent of the amount of RNA retained on a filter in a reference binding solution) following loading of various binding solutions. All of the binding solutions contained radioactively labeled AUUUA RNA either alone or including various other components. The first column represents a binding solution without RNA binding protein. The remaining columns represent binding solution containing RNA binding protein (K562 extract). Columns 3 through 8 correspond to binding solutions including the indicated test compound.
Figure 5:
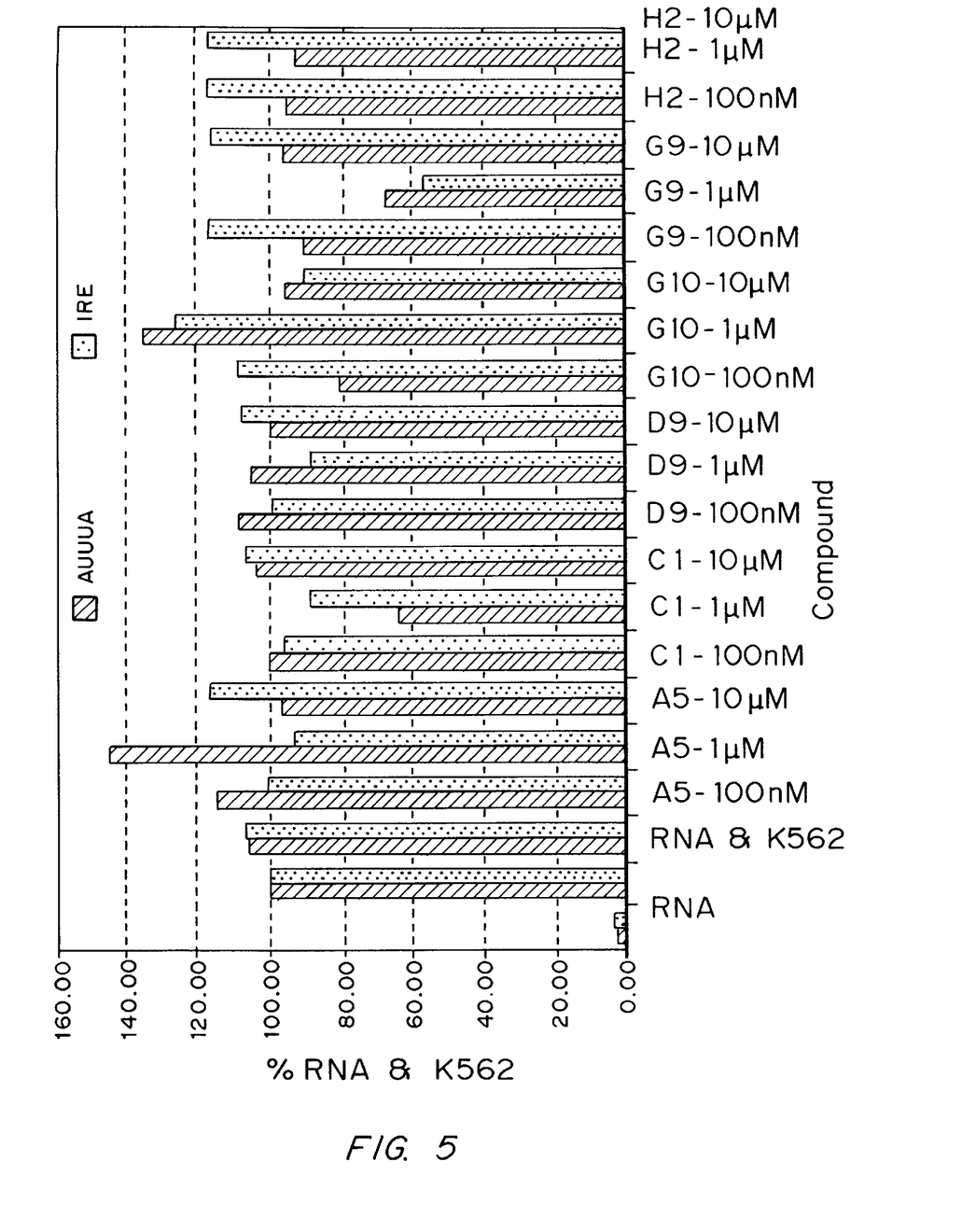
FIG. 5 is a graph of the amount of radioactively labeled RNA retained on a filter (expressed in percent of the amount of RNA retained on a filter in a reference binding solution) following loading of various binding solutions. Alternate columns correspond to binding solutions containing radioactively labeled AUUUA RNA or IRE RNA, either alone or including various other components. The first two column represents binding solutions without RNA binding protein. The remaining columns represent binding solution containing RNA binding protein (K562 extract). Columns 5 through 40 correspond to binding solutions including the indicated amount of the indicated test compound.

Seventeen compounds were chosen for further analysis at 100 nM, 1 μM and 10 μM using both AUUUA and IRE RNAs based on the results from three screening efforts (Exps. 29–31). Table 1 summarizes the results from these compounds at 10 μM. The results are also shown graphically in FIG. 4. Compound C1 was consistently the most active inhibitor resulting in close to a 50% reduction in counts (p=0.001) while A5 was the most active enhancer increasing counts by 38% over controls (p<0.001). Compound G10, CNI-1493, produced a substantial increase in counts in 3 of the 4 experiments. Compounds D9 and H2, chosen as negative controls from the initial screening, continued to have no effect in the dose dependent screen (Exp. 33) and were identified as vehicle controls. When the 17 compounds were screened against IRE RNA, a differential effect was seen with compound A5 (see FIG. 5). This most efficacious enhancer of AUUUA binding failed to have an effect on IRE.

Example 3

Identification of RNA Binding Protein Binding Sites

The following example illustrates the manner of identifying putative binding sites for RNA binding proteins

TABLE 1

| Compound | Experiment # | | | | Compound | Avg. % | SEM |
| --- | --- | --- | --- | --- | --- | --- | --- |
| | #33 | #31 | #30 | #29 | | | |
| RNA | 1.84 | 2.57 | 1.98 | 1.48 | RNA | 1.97 | 0.28 |
| RNA & K562 | 100.00 | 100.00 | 100.00 | 100.00 | RNA & K562 | 100.00 | |
| A3-10 µM | 103.79 | 67.58 | 92.35 | 82.69 | A3-10 µM | 86.60 | 7.69 |
| A4-10 µM | 104.74 | 93.36 | 62.58 | 98.27 | A4-10 µM | 89.74 | 9.35 |
| A5-10 µm | 144.10 | 145.00 | 133.15 | 130.31 | A5-10 µm | 138.14 | 3.75 |
| A11-10 µm | 101.75 | 96.59 | 76.95 | 82.91 | A11-10 µm | 89.55 | 5.78 |
| C1-10 µm | 64.52 | 39.48 | 43.08 | 68.93 | C1-10 µm | 54.00 | 7.44 |
| C8-10 µm | 104.98 | 79.45 | 85.32 | 79.37 | C8-10 µm | 86.53 | 6.42 |
| D9-10 µm | 105.10 | 105.54 | 100.69 | 99.68 | D9-10 µm | 102.75 | 1.50 |
| E7-10 µm | 99.20 | 87.16 | 74.40 | 93.46 | E7-10 µm | 88.56 | 5.32 |
| F6-10 µm | 100.10 | 82.17 | 57.89 | 85.68 | F6-10 µm | 81.46 | 8.76 |
| G1-10 µm | 89.62 | 80.62 | 94.23 | 80.16 | G1-10 µm | 86.16 | 3.46 |
| G6-10 µm | 91.49 | 85.57 | 92.72 | 80.41 | G6-10 µm | 87.55 | 2.85 |
| G7-10 µm | 94.62 | 82.06 | 62.38 | 79.87 | G7-10 µm | 79.73 | 6.63 |
| G9-10 µm | 68.52 | 81.48 | 74.65 | 67.25 | G9-10 µm | 72.98 | 3.26 |
| G10-10 µm | 135.24 | 127.28 | 66.94 | 114.53 | G10-10 µm | 111.00 | 15.29 |
| G11-10 µm | 93.50 | 87.91 | 88.39 | 85.17 | G11-10 µm | 88.74 | 1.74 |
| G12-10 µm | 93.56 | 86.39 | 86.37 | 84.10 | G12-10 µm | 87.60 | 2.06 |
| H2-10 µm | 93.39 | 97.31 | 103.77 | 95.65 | H2-10 µm | 97.58 | 2.20 |

Analysis

Competition studies have been performed using the filter assay in which unlabeled wild-type or mutant RNA is added to the reaction at 100 to 10,000 times the concentration of $^{32}$P-RNA to compete for the protein binding of the radiolabeled RNA. It has been demonstrated the high-throughput assay can be used effectively for this type of study using a variety of RNA molecules including IRE, AUUUA, APP, U1, and His. Using IRE, a concentration dependent inhibition of binding by unlabeled wild-type RNA has been shown, with no effect of shown by unlabeled mutant RNA, except at the highest concentration. These results have been confirmed by gel shift analysis. Furthermore, the disclosed assay can be used to detect more subtle differences in the ability of various RNA molecules to bind protein as demonstrated by the results of the U1 and His experiments. In this case, the mutant RNA has a weak binding affinity for the RNA binding protein. When unlabeled mutant RNA is added to the binding reaction, a slight concentration dependent inhibition is detected with maximum inhibition of 50 to 70% occurring at 10,000 times the $^{32}$P-RNA concentration. In this way, the binding affinity of various altered forms of the binding site of an RNA binding protein can be compared.

A 96 member random compound library was screened with the disclosed high throughput assay. The compounds were initially screened at 10 µM against $^{32}$P-labeled AUUUA RNA. One compound was found to produce a significant increase in detectable counts while two compounds were found to produce a significant decrease in counts. Seventeen compounds were chosen for further analysis at 100 nM, 1 µM and 10 µM using both AUUUA and IRE RNA molecules to determine if any selectivity of the compounds could be detected. When the 17 compounds were screened against IRE RNA, a differential effect was seen with the enhancing compound. The most efficacious enhancer of AUUUA binding failed to have an effect on IRE. Gel shifts of these compounds using AUUUA RNA confirmed the activity of the inhibitors.

present in a nucleotide sequence database and confirmation that some identified nucleotide sequences do interact with RNA binding proteins.

The GenBank nucleotide sequence database was searched for the presence of the sequence for amyloid precursor protein (APP). The human sequences were chosen for further analysis in part because such human sequences are of most practical interest. In general, human sequences identified in such searches are preferred. Of the 17 sequences meeting the above criteria, 8 of the sequences (accession numbers Y00264, X13475, M16765, X06989, M34873, D87675, M28373, and M18734) contained sequences encompassing the coding region and/or 3'-UTR. The nucleotide sequences of the coding region fragment and the two 3'-UTR fragments are shown in SEQ ID NOs: 1–3.

A primer pair was designed for SEQ ID NO:1 which used a sense primer beginning at nucleotide 1381 and an antisense primer beginning at nucleotide 1505 (accession #Y00264). A primer pair was designed for SEQ ID NO:2 which used a sense primer beginning at nucleotide 2679 and an antisense primer beginning at 2780 (accession #Y00264). A primer pair was designed for sequence 3 which used a sense primer beginning at nucleotide 3055 and an antisense primer beginning at nucleotide 3193 (accession #Y00264). In addition, the 5' primers contained 24 nucleotides at the 5' end encoding for the T7 promoter. Clones containing the above sequences were generated by PCR from a plasmid containing the human APP cDNA. The clones were restriction mapped and analyzed by gel electrophoresis to confirm their identity.

PCR products generating a single band (in the undigested lanes) were then used for in vitro transcription of labeled RNA using Promega's RiboProbe kit. The labeled transcripts were used in the RNA binding protein detection assay described above. The binding solutions containing the labeled RNA were incubated with 0.5 µg of protein isolated from the lymphoblastoma cell line K562 and the neuroblastoma cell line SH-SY5Y (SEQ ID NOs:1 and 2 only), and the products were resolved on a non-denaturing gel. Labeled RNAs which exhibited binding activity were then used in a second experiment in which a 10, 100 and 1,000 fold molar excess of unlabeled identical RNA or the same excess of different RNA are added to the binding reactions. A concentration dependent inhibition of complex formation was observed with specific competitor while not competition was seen when the mutant RNA was added in excess.

The GenBank nucleotide sequence database was searched for the presence of the sequence for interleukin 10 (IL10). The human sequence with accession number M57627 contained the sequence of the full-length 3'-UTR. The nucleotide sequence of this UTR is shown in SEQ ID NO:4.

A primer pair was designed which used a sense primer beginning at the 3' end of the coding region, nucleotide 559, and oligo(dT)$_{18}$ as the antisense primer. In addition, the sense primer contained 24 nucleotides encoding for the T7 promoter at the 5' end. Clones containing the above sequences were generated by RT-PCR from total RNA obtained from the K562 lymphoblastoma cell line. The clones were restriction mapped and analyzed by gel electrophoresis to confirm their identity.

PCR products generating a single band (in the undigested lanes) were then used for in vitro transcription of labeled RNA using Promega's RiboProbe kit. The labeled transcripts were used in the RNA binding protein detection assay described above. The binding solutions containing the labeled RNA were incubated with 0.5 µg of protein isolated from the same cell from which the RT-PCR product was generated, and the products were resolved on a non-denaturing gel. Labeled UTRs which exhibit binding activity were then used in a second experiment in which a 10, 100 and 1,000 fold molar excess of unlabeled identical RNA or the same excess of different RNA are added to the binding reactions. A concentration dependent inhibition of complex formation was observed with specific competitor while not competition was seen when the mutant RNA was added in excess.

The GenBank nucleotide sequence database was searched for the presence of the sequence for erb-B2. The human sequence with accession number X03363 contained the sequence of the full-length 3'-UTR. The nucleotide sequence of this UTR is shown in SEQ ID NO: 5.

A primer pair was designed which used a sense primer beginning at nucleotide 4203 and an antisense primer beginning at nucleotide 4473. In addition, the sense primer contained 24 nucleotides encoding for the T7 promoter at the 5' end. Clones containing the above sequences were generated by RT-PCR from total RNA obtained from the K562 lymphoblastoma cell line. The clones were restriction mapped and analyzed by gel electrophoresis to confirm their identity.

PCR products generating a single band (in the undigested lanes) were then used for in vitro transcription of labeled RNA using Promega's RiboProbe kit. The labeled transcripts were used in the RNA binding protein detection assay described above. The binding solutions containing the labeled RNA were incubated with 0.5 µg of protein isolated from the same cell from which the RT-PCR product was generated, and the products were resolved on a non-denaturing gel. Labeled UTRs which exhibit binding activity were then used in a second experiment in which a 10, 100 and 1,000 fold molar excess of unlabeled identical RNA or the same excess of different RNA are added to the binding reactions. A concentration dependent inhibition of complex formation was observed with specific competitor while not competition was seen when the mutant RNA was added in excess.

The sequence for the 5' UTR of the human IGFI-R has been published by two independent laboratories, Cooke et al., "Analysis of the human type I IGFI-R promoter region" *Biochem. Biophys. Res. Comm.* 177:1113–1120 (1991), and Mamula and Goldfine, "Cloning and characterization of the Human IGFI-R gene 5'-flanking region" *DNA and Cell Biol.* 11:43–50 (1992). Probes corresponding to regions of the IGFI-R 5'UTR were prepared from an IGFI-R Charon 21A clone, R737P3. This clone contained a 3.5 kB HindIII fragment from a human genomic chromosome 15 library (American Type Culture Collection, #57737) that included the 5' flanking region and first exon of the type I IGFI-R gene.

Polymerase chain reaction (PCR) was used to generate a series of overlapping DNA fragments, of approximately 200 nucleotides in length, spanning the 1.1 kB 5' UTR. This size was chosen in order to generate fragments that would be large enough to contain significant secondary structure, but small enough to resolve well in a mobility shift assay. The sense primers for these PCR reactions contained a T7 RNA polymerase consensus sequence. The PCR fragments served as templates for in vitro transcription of $^{32}$P UTP labeled RNA probes in a Riboprobe In Vitro Transcription System T7 Kit (Promega). Unincorporated nucleotides were removed with an RNeasy Mini Kit (Qiagen).

The labeled transcripts were used in the RNA binding protein detection assay described above. The binding solutions containing the labeled RNA were incubated with 0.5 µg of protein isolated from the mammalian cell line COS1, and the products were resolved on a non-denaturing gel. Labeled RNA's which exhibited binding activity were then used in a second experiment in which a 10, 100 and 1,000 fold molar excess of unlabeled identical RNA or the same excess of different RNA are added to the binding reactions. A concentration dependent inhibition of complex formation was observed with specific competitor while not competition was seen when the mutant RNA was added in excess.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of using a nucleic acid sequence to identify compounds having an effect on interactions between an RNA binding protein and an RNA molecule comprising the nucleic acid sequence by
    detecting interactions between the RNA binding protein and the RNA molecule in the presence of a test compound and in the absence of the test compound,
    wherein the nucleic acid sequence is SEQ ID NO:1, SEQ ID NO:2, SEQ ID NO:3, SEQ ID NO:4, SEQ ID NO:5, or SEQ ID NO:6.

2. The method of claim 1 wherein the method comprises
    (a) forming a set of one or more test solutions, wherein each test solution comprises the RNA molecule and buffer components, wherein the buffer components comprise a buffer, a monovalent cation, a divalent cation, a reducing agent, and a density agent,
    (b) heating the test solutions for a time and to a temperature sufficient to denature the RNA molecule,
    (c) cooling the test solutions,
    (d) adding the RNA binding protein to the test solutions,
    (e) detecting interactions between the RNA molecule and the RNA binding protein in the test solutions,
        wherein one of the test compounds is added to each test solution during or following any of steps (a) through (d),
        wherein the method further comprises, prior to, simultaneous with, or following steps (a) through (e),
    (f) forming a control solution comprising the RNA molecule and the buffer components, wherein the control solution does not contain any of the test compounds,
    (g) heating the control solution for a time and to a temperature sufficient to denature the RNA molecule,
    (h) cooling the control solution,
    (i) adding the RNA binding protein to the control solution, and
    (j) detecting interactions between the RNA binding protein and the RNA molecule in the control solution,
        wherein a test compound is identified as a compound having an effect on interactions between the RNA molecule and the RNA binding protein if the interactions detected in the control solution and the interactions detected in the test solution containing the test compound differ.

3. The method of claim 1 wherein the nucleic acid sequence is not operatively linked to a protein encoding nucleotide sequence to which the nucleotide sequence is naturally linked.

4. The method of claim 1 further comprising forming a composition for affecting expression of a gene that encodes the nucleic acid sequence comprising mixing at least one test compound identified as having an effect on interactions between the RNA molecule and the RNA binding protein with a pharmaceutically acceptable carrier.

5. The method of claim 4 further comprising administering the composition to an individual or a cell in need of altered expression of the gene.

6. The method of claim 5 further comprising delivering at least one test compound identified as having an effect on interactions between the RNA molecule and the RNA binding protein to a cell in need of altered expression of the gene.

7. A nucleic acid molecule comprising a nucleotide sequence, wherein the nucleotide sequence is not operatively linked to a protein encoding nucleotide sequence to which the nucleotide sequence is naturally linked, wherein the nucleotide sequence is SEQ ID NO:1, SEQ ID NO:2, SEQ ID NO:3, SEQ ID NO:4, SEQ ID NO:5, SEQ ID NO:6, the corresponding DNA sequence of SEQ ID NO:1, the corresponding DNA sequence of SEQ ID NO:2, the corresponding DNA sequence of SEQ ID NO:3, the corresponding DNA sequence of SEQ ID NO:4, the corresponding DNA sequence of SEQ ID NO:5, or the corresponding DNA sequence of SEQ ID NO:6.

8. The nucleic acid molecule of claim 7 wherein the nucleic acid molecule is an RNA molecule or can be transcribed into an RNA molecule, wherein the RNA molecule does not contain a protein encoding nucleotide sequence to which the nucleotide sequence is naturally linked.

9. The nucleic acid molecule of claim 7 wherein the nucleic acid molecule is an RNA molecule.

10. A method for identifying RNA binding proteins that interact with nucleic acid segments, the method comprising detecting interactions between an RNA binding protein and an RNA molecule, wherein the RNA molecule includes the nucleic acid segment, wherein the nucleic acid segment consists of the nucleotide sequence identified as SEQ ID NO:1, SEQ ID NO:2, SEQ ID NO:3, SEQ ID NO:4, SEQ ID NO:5 or SEQ ID NO:6, wherein detection of interactions between the RNA binding protein and the RNA molecule identifies the RNA binding protein as an RNA binding protein that interacts with the nucleic acid segment.

11. The nucleic acid molecule consisting of the nucleotide sequence of SEQ ID NO:6.

12. The nucleic acid molecule of claim 7, wherein said nucleic acid molecule is operably linked to a heterologous nucleic acid sequence.

13. The nucleic acid molecule of claim 12, wherein said heterologous nucleic acid sequence is a gene used to monitor the binding of an RNA binding protein to a nucleic acid molecule of claim 7.

* * * * *

SEQUENCE LISTING

<160> NUMBER OF SEQ ID NOS: 11

<210> SEQ ID NO 1
<211> LENGTH: 125
<212> TYPE: RNA
<213> ORGANISM: Artificial Sequence

```
<220> FEATURE:
<223> OTHER INFORMATION: Synthetic

<400> SEQUENCE: 1
ccucgucacg uguucaauau gcuaaagaag uauguccgcg cagaacagaa ggacagacag      60
cacacccuaa agcauuucga gcaugugcgc augguggauc ccaagaaagc cgcucagauc     120
cgguc                                                                125

<210> SEQ ID NO 2
<211> LENGTH: 102
<212> TYPE: RNA
<213> ORGANISM: Artificial Sequence
<220> FEATURE:
<223> OTHER INFORMATION: Synthetic

<400> SEQUENCE: 2
uccuuuccug aucacuaugc auuuaaagu uaaacauuuu uaaguauuuc agaugcuuua       60
gagagauuuu uuuuccauga cugcauuuua cuguacagau ug                       102

<210> SEQ ID NO 3
<211> LENGTH: 139
<212> TYPE: RNA
<213> ORGANISM: Artificial Sequence
<220> FEATURE:
<223> OTHER INFORMATION: Synthetic

<400> SEQUENCE: 3
gaucgcuuuc uacacuguau uacauaaaua auuaaauaa aauaaccccg ggcaagacuu       60
uucuuugaag gaugacuaca gacauuaaau aaucgaagua auuuuggguag gggagaagag    120 gcagauucaa uuuucuuua                                                 139

<210> SEQ ID NO 4
<211> LENGTH: 1043
<212> TYPE: RNA
<213> ORGANISM: Artificial Sequence
<220> FEATURE:
<223> OTHER INFORMATION: Synthetic

<400> SEQUENCE: 4
cgaaacugag acaucagggu ggcgacucua uagacucuag gacauaaauu agaggucucc      60
aaaaucggau cugggcucu gggauagcug acccagcccc uugagaaacc uuauuguacc      120
ucucuuauag aauauuuauu accucugaua ccucaaccc cauuucuauu uauuuacuga      180
gcuucucugu gaacgauuua gaaagaagcc caauauuaua auuuuuuca auauuuauua      240 uuuucaccug uuuuuaagcu guuccauag ggugacacac uaugguauuu gaguguuuua      300
agauaaauua uaaguuacau aagggaggaa aaaaauguu cuuggggag ccaacagaag       360 cuuccauucc aagccugacc acgcuuucua gcuguugagc uguuuccu gaccuccuc        420 uaauuuaucu ugucucuggg cuuggggcuu ccuaacugcu acaaauacuc uuaggaagag     480
aaaccaggga gccccuuuga ugauuaauuc accuuccagu gucucggagg gauucccua      540 accucauucc caaccacuu cauucuugaa agcugguggcc agcuguuau uuauaacaac      600 cuaaauuugg uucuaggccg ggcgcggugg cucacgccug uaauccagc acuugggag       660 gcugaggcgg guggaucacu ugaggucagg aguuccuaac cagccuggcu aacaugguga    720
aaccccgucu cuacuaaaaa uacaaaaauu agccgggcau gguggcgcg accuguaauc     780 ccagcuacuu gggaggcuga ggcaagagaa uugcuugaac caggagaug gaaguugcag     840
```

```
ugagcugaua ucaugccccu guacuccagc cugggugaca gagcaagacu cugucucaaa    900
aaaauaaaaa uaaaaauaaa uuugguucua auagaacuca guuuaacua gaauuuauuc    960 aauuccucug ggaauguuac auuguuuguc ugucuucaua gcagauuuua auuugaaua   1020 aauaaaugua ucuuauucac auc                                          1043

<210> SEQ ID NO 5
<211> LENGTH: 271
<212> TYPE: RNA
<213> ORGANISM: Artificial Sequence
<220> FEATURE:
<223> OTHER INFORMATION: Synthetic

<400> SEQUENCE: 5
uggaugccac agcccagcuu ggcccuuucc uuccagaucc uggguacuga aagccuuagg     60
gaagcuggcc ugagagggga agcggcccua agggagyguc uaagaacaaa agcgacccau   120
ucagagacug ucccugaaac cuaguacugc cccccaugag gaaggaacag caauggoguc   180 aguauccagg cuuuguacag agugcuuuuc uguuuaguuu uuacuuuuuu uguuuuguuu   240
uuuuaaagau gaaauaaaga cccaggggga g                                 271

<210> SEQ ID NO 6
<211> LENGTH: 316
<212> TYPE: RNA
<213> ORGANISM: Artificial Sequence
<220> FEATURE:
<223> OTHER INFORMATION: Synthetic

<400> SEQUENCE: 6
cggcgggagu gcugagcgcg gcgcggccgg cccgccgcuu ugugugyguc cuggauuugg     60
gaaggagcuc gccgcggcgg cggcgcugag ggaggaggcg gcggcgagcg gagccaggag   120
gaggaggagg aggaggggga gccgcucauu cauuuugacu ccgcguuucu gccccucgcc   180
ggccucgccu gugacccgga cuucgggggcg aucuugcgaa cugcgucgcg cccucccgcg   240
gcggaagcuc gggcgyccgg ccgccucccg cgcgccaggg ccgggcuugu uuuccucgc   300 cuaggcagau uugggc                                                  316

<210> SEQ ID NO 7
<211> LENGTH: 272
<212> TYPE: RNA
<213> ORGANISM: Artificial Sequence
<220> FEATURE:
<223> OTHER INFORMATION: Synthetic

<400> SEQUENCE: 7
ggggcgggcc aauggcggcg guccauaaa aaggcagcuc cgcgcgcucu cuuccuaaga     60
acacaagaau cccuugugga gugucgguuu agguugcagg gucuuaagug agucagggcg   120
cggagguccg gcgggagacg caucgucaca gaacguccau ucuccguuuc acagcccgca   180
cagcuugagc cucgagcgca gcgcggccau ggagcccagc agcaagaagg ugacgggccg   240
ccuuauguug gccgugggag gggcagugcu cg                                272

<210> SEQ ID NO 8
<211> LENGTH: 21
<212> TYPE: RNA
<213> ORGANISM: Artificial Sequence
<220> FEATURE:
<223> OTHER INFORMATION: Synthetic
```

-continued

```
<400> SEQUENCE: 8
auuuauuuau uuauuuauuu a                                              21

<210> SEQ ID NO 9
<211> LENGTH: 35
<212> TYPE: RNA
<213> ORGANISM: Artificial Sequence
<220> FEATURE:
<223> OTHER INFORMATION: Synthetic

<400> SEQUENCE: 9
ggagcguacg cgagcuacag gcucgcguac gcucc                               35

<210> SEQ ID NO 10
<211> LENGTH: 21
<212> TYPE: RNA
<213> ORGANISM: Artificial Sequence
<220> FEATURE:
<223> OTHER INFORMATION: Synthetic

<400> SEQUENCE: 10
aauccauugc acuccggauu u                                              21

<210> SEQ ID NO 11
<211> LENGTH: 26
<212> TYPE: RNA
<213> ORGANISM: Artificial Sequence
<220> FEATURE:
<223> OTHER INFORMATION: Synthetic

<400> SEQUENCE: 11
aaaaaggcuc uuuucagagc caccca                                         26
```